United States Patent [19]

Kossoff et al.

[11] 4,031,743
[45] June 28, 1977

[54] ULTRASONIC ECHOGRAM DISPLAY

[75] Inventors: George Kossoff, Northbridge; David Errol Robinson, Avalon Beach, both of Australia

[73] Assignee: The Commonwealth of Australia, c/o Dept. of Health, Phillip, Australia

[22] Filed: Jan. 15, 1976

[21] Appl. No.: 649,347

Related U.S. Application Data

[63] Continuation-in-part of Ser. No. 466,791, May 3, 1974, abandoned.

[30] Foreign Application Priority Data

May 3, 1973 Australia .............................. 3195/73

[52] U.S. Cl. ...................... 73/67.8 R; 343/5 SM; 340/1 R

[51] Int. Cl.² ..................... G01S 9/66; G01N 29/04

[58] Field of Search ............... 340/1 R; 343/5 SM; 73/67.7, 67.8 R, 67.8 S, 67.9

[56] References Cited

UNITED STATES PATENTS

| | | | |
|---|---|---|---|
| 3,033,029 | 5/1962 | Weighart | 73/67.8 |
| 3,348,410 | 10/1967 | Henry | 73/67.8 |
| 3,367,173 | 2/1968 | Uphoff | 73/67.8 |

*Primary Examiner*—Richard A. Farley

[57] ABSTRACT

A method of pulse-echo ultrasonic examination of an object particularly in medical diagnostic examination, comprises the stepwise increase of the gain of the equipment to compensate for loss of energy as echoes are received from reflecting surfaces deeper within the object and cyclic alteration of the gain at each step.

6 Claims, 5 Drawing Figures

ULTRASONIC ECHOGRAM DISPLAY

CROSS REFERENCE OF RELATED APPLICATION

This is a Continuation-In-Part of copending U.S. application Ser. No. 446,791, filed May 3, 1974 and now abandoned.

This invention relates to the technique of ultrasonic echoscopy of objects and in particular to an extension of known techniques of ultrasonic echoscopy to provide more useful information concerning the examined objects. It is particularly, but not solely, directed to the more effective acquisition of data in medical diagnosis utilising this technique.

Ultrasonic echoscopy provides information about an examined object which may be displayed in the form of an ultrasonic echogram. Such an echogram consists of a display of acoustic impedance discontinuities or reflecting surfaces in the object. It is obtained by directing a short pulse of ultrasonic energy, typically in the 1-30 MH z frequency range generated for example by a transducer into the examined object where any acoustic impedance discontinuities in the object reflect some of the energy in the form of an echo. This echo is received, for example by a transducer, converted into an electric signal and displayed as an echogram on a cathode ray oscilloscope, a film, a chart or the like.

The echogram may constitute either a one dimensional or a two dimensional representation and in both cases the information is contained in the position and magnitude of the echo displayed. In a one dimensional display, the position along a base line is used to indicate the distance to the reflecting surface whilst the magnitude of the echo is displayed, for example, as a deflection of a base line or as an intensity change. In a two dimensional display, the position along a base line is used to indicate the distance to the reflecting surface as in a one dimensional display, and the direction of the base line is used to represent the direction of propagation of the acoustic energy. The two dimensional display is obtained by changing this direction of propagation of the acoustic energy and by instituting a similar but not necessarily identical movement of the base line of the display. The magnitude of the echo is displayed as for a one dimensional display; for example, as a deflection of the base line or as an intensity change.

The technique of ultrasonic echoscopy is used in medical diagnosis to obtain information about the anatomy of patients. The application of the technique is now widely investigated and is described, for example, by D. E. Robinson in Proceeding of the Institution of Radio and Electronics Engineers, Australia, Vol. 31, No. 11, pages 385 – 392, November, 1970; "The Application of Ultrasound in Medical Diagnosis". As pointed out in this article, ultrasonic echoscopy may be used to produce displays resembling anatomical cross-sections which have proved clinically useful when the desired information concerns physical dimensions, shapes of organs or structures or the like. Ultrasonic echography has proved of particular value as a diagnostic aid in the abdomen and pregnant uterus, eye, breast, brain, lung, kidney, liver and heart, these being areas of soft tissue with little bone and air. In general, the technique is considered to complement other techniques to provide a more complete picture of the patient's condition, however particularly in pregnancies, ultrasonic echoscopy may be useful in place of X-rays where the latter may not give sufficient information or may be dangerous. In medical use, a pulse of ultrasonic energy is transmitted into a patient in a known direction and echoes are received from reflecting surfaces within the body. The time delay between a transmitted pulse and the received echo depends on the distance from the transmitter to the reflecting surface and the distance information so obtained may be displayed in a suitable way for interpretation and clinical use as a one dimensional range reading or as a two dimensional cross section as previously described.

If a pulse of ultrasound is propagated into a medium, echoes will be received at various time delays and these time delays will be proportional to the distances from the transducer producing the pulse to the interface provided the velocity of propagation is constant. In soft tissues found in the human body the velocity of sound is reasonably constant and pulsed ultrasound provides a convenient method of measuring the depth of a particular structure from the transducer face without inconvenience to the patient. This information can be used in a number of ways.

In the simplest form of display, "A mode", the echoes are presented as deflections of the trace of an oscilloscope in which distance is represented along the time axis. This mode is useful clinically when the source of the various echoes displayed can be positively identified. It is possible to measure the distance between two echoes or between the energising pulse and an echo with accuracy but it may not be possible to identify the source of the echoes. It has been used to measure the size of the baby's head inside the uterus, the depth of the eye and the bladder and to locate the midline of the brain. Similar information may be displayed by use of the "B mode" where a cross sectional view is obtained by moving the transducer around the examined object and making the trace on the display follow a similar movement. A, B mode display may be obtained either with simple or compound scanning. In the former the movement of the transducer is selected so that there is no superpositioning of lines of sight from different directions. Linear and sector scanning are typical examples of simple scanning. With compound scanning the movement of the transducer is selected so that there is superposition from different lines of sight, a combination of linear and sector scanning being a typical example of a compound scan.

If the interface of interest is moving, its position may be plotted with time ("M mode") by using the B mode presentation and allowing the time base to be swept at right angles to its direction so as to display the movements of the interface echo backwards and forwards along the time base. This is used to demonstrate the pulsatile movements of various parts of the heart and brain. If the B mode is used but the trace on the screen is made to represent the line of sight of the transducer and then the transducer is scanned around the patient and the time base line on the screen made to follow, a two-dimensional plot of impedance discontinuities is obtained. Two dimensional visualisation has been used in the pregnant uterus, abdomen, eye and breast.

Coupling from the transducer to the patient may be achieved by skin contact or by use of a water delay bath. If a water delay bath is used the distance between the transducer and the skin surface must be greater than the largest depth of penetration to be used, to avoid ambiguity due to multiple reflection. In general the skin contact scan results in greater comfort for the patient and echograms of less clarity while the water delay scan gives less patient comfort and better quality echograms.

In order to compensate for the reduction in the energy of the ultrasonic pulse due to attenuation within the object under examination for example tissue, the gain of the receiver is generally increased as the echo of the pulse is received from deeper reflecting surfaces within the object. This type of increase in gain is generally referred to as "time gain compensation" or "TGC". In some receivers, TGC amplification is also followed by a non-linear compression amplification to further compress the size of the echoes so that they may be more readily displayed on the display unit. The compression and display systems are non-linear, and therefore only qualitative information on echo size is displayed.

It is an object of the present invention to provide a method whereby the information obtained by ultrasonic echoscopic techniques may be made available in a more useful form, especially for medical diagnosis and the like. In particular, an object of the invention is to provide a method whereby the relative strengths of echoes can be measured directly from the display screen.

A method of ultrasonic examination of an object according to the known art comprises the steps of transmitting pulses of ultrasonic energy into the object and receiving echoes of said pulses of ultrasonic energy reflected by acoustic impedance discontinuities within the object, the echoes reflected by acoustic impedance discontinuities being received by receiver means, the gain of which is increased in predetermined steps to compensate for attenuation of said echoes within the object. The gain controlled signals are then further processed and displayed in one of a number of ways described above.

To this known method, is added a cyclic gain control which varies the gain of the system up and down around the average controlled gain value. By this method, changes in echo strength can be measured accurately on a logarithmic scale without being affected by non-linearity of the compression amplifier and display system.

It will thus be apparent that the invention relates to the display of ultrasonic echoes where the gain of the equipment is altered step wise to compensate for loss of energy as echoes are received from deeper structures. In its preferred aspect, the invention utilises a stepped gain TGC amplifier where steps of known and selectable gain and duration are employed to compensate for attenuation by tissue. To this stepped gain is added a cyclically changing gain stage which varies the overall gain around the value set to compensate for average attenuation. By way of example, the latter may be obtained by cyclically changing the gain in say steps of 2dB every 2mm, this gain variation being superimposed on the more slowly increasing gain of the TGC amplifier.

One of the main purposes of the invention is to allow measurement of distance between echoes displayed as of equal strength at penetrations where the gain of the receiver differs by the known stepped amount. The difference in echo strength with penetration in signals originating from similar discontinuities is due to attenuation. Since all other factors are kept equal the difference in gain for echoes displayed as of equal strength compensates exactly for the attenuation and the attenuation rate is therefore given by $$\text{Attenuation rate} = \frac{\text{Difference in Gain}}{\text{Distance between echoes}}$$

The invention is illustrated in the accompanying diagrams in which:

FIG. 1 represents the monotonically rising time varied gain characteristic of the receiver according to the known art, FIG. 2 represents the cyclically varying gain characteristic to be added according to the instant invention, FIG. 3 represents the gain characteristic consisting of the combined operation of the characteristics in FIG. 1 and FIG. 2, FIG. 4 represents typical application of the invention, FIG. 5 is a block diagram of an implementation of a preferred embodiment of the invention.

In FIG. 1 the gain of the amplifier is plotted as a function of distance into the patient, which corresponds with the delay time of returned echoes. This corresponds to the time-gain-controlled amplification commonly used in the art. By way of an example, the steps in the gain are at 1cm intervals of distance and 4dB intervals of gain. These parameters would need to be changed according to the precise type of tissue being examined and ultrasonic frequency being used. With a small increase of complexity of the analysis step a smooth curve of gain increase could be used such as is normally used in the art.

Figure 4:
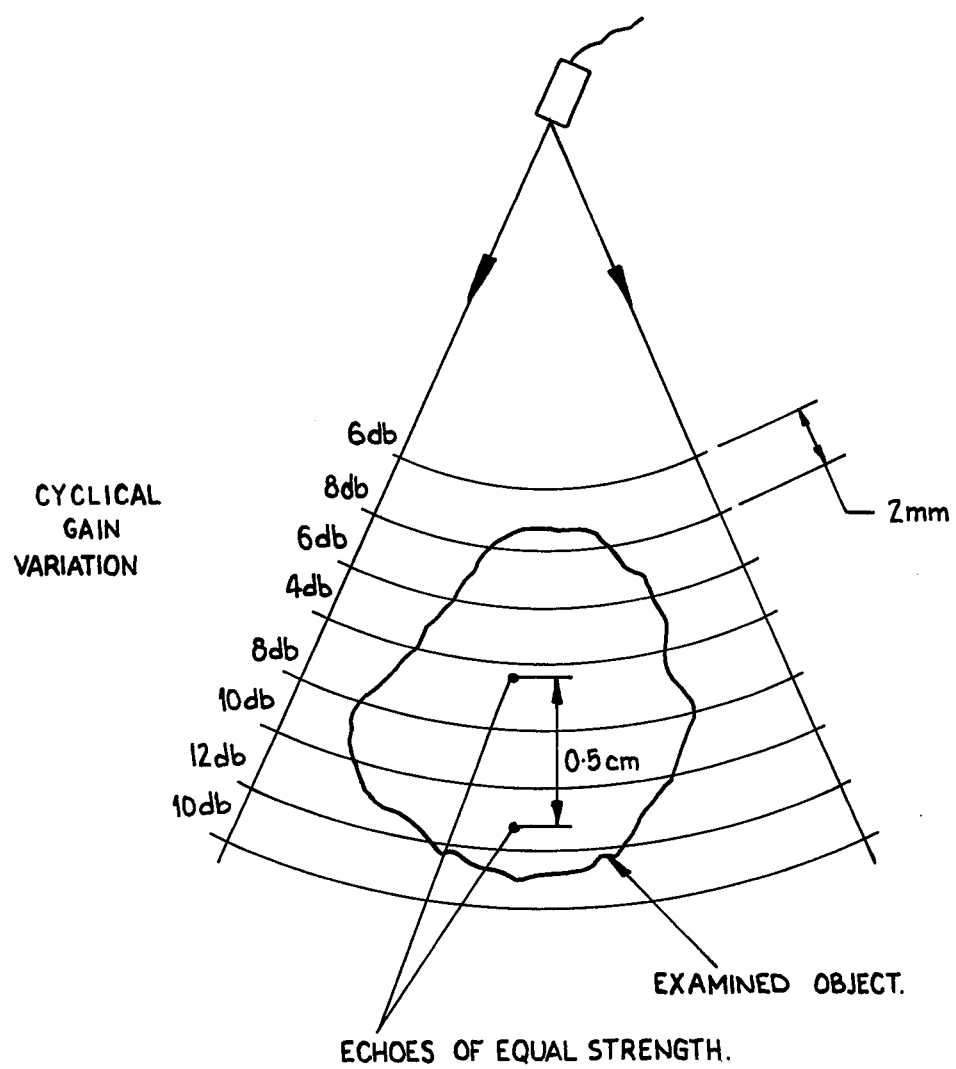

FIG. 4 shows an example of the invention in use and represents a display of the screen representing a sector scan. The action of the cyclical gain variation is to produce lighter and darker bands across the picture. Within the examined object diffuse echoes are received which are displayed as a shade of grey. To measure the effective attenuation rate of the ultrasound two points of equal apparant strength are located. The attenuation rate is calculated from the known difference in gain and the distance between echoes as taught in the present invention. In this example $$\text{Attenuation rate} = \frac{\text{Difference in gain}}{\text{Distance between echoes}}$$

$$= \frac{6db}{0.5 \text{ cm}}$$

$$= 12 \text{ db/cm}$$

Figure 1:
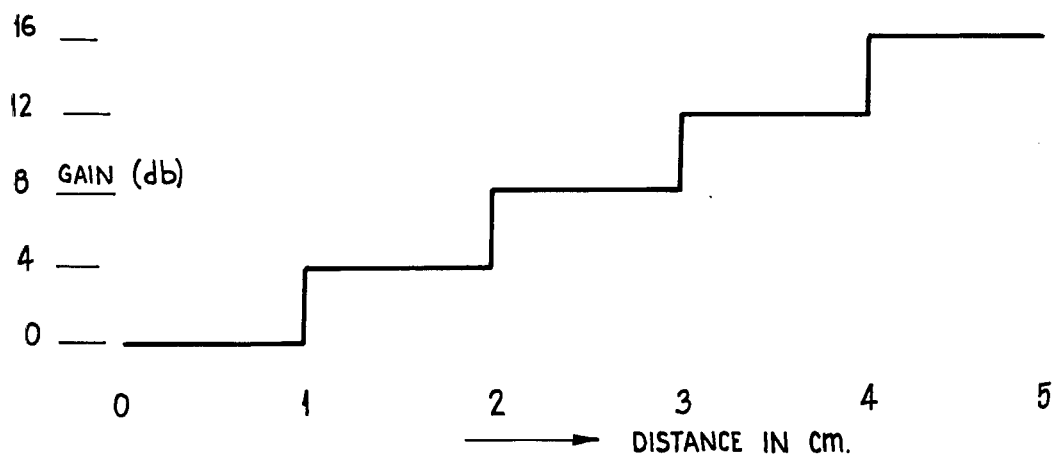
Figure 2:
FIG. 2 illustrates the more rapid varying cyclic gain control according to the instant invention; by way of example in this Figure there are five different gain levels during each step of the time-gain-controlled characteristics, however it will be appreciated that other cyclic variations may be employed if desired.
Figure 3:
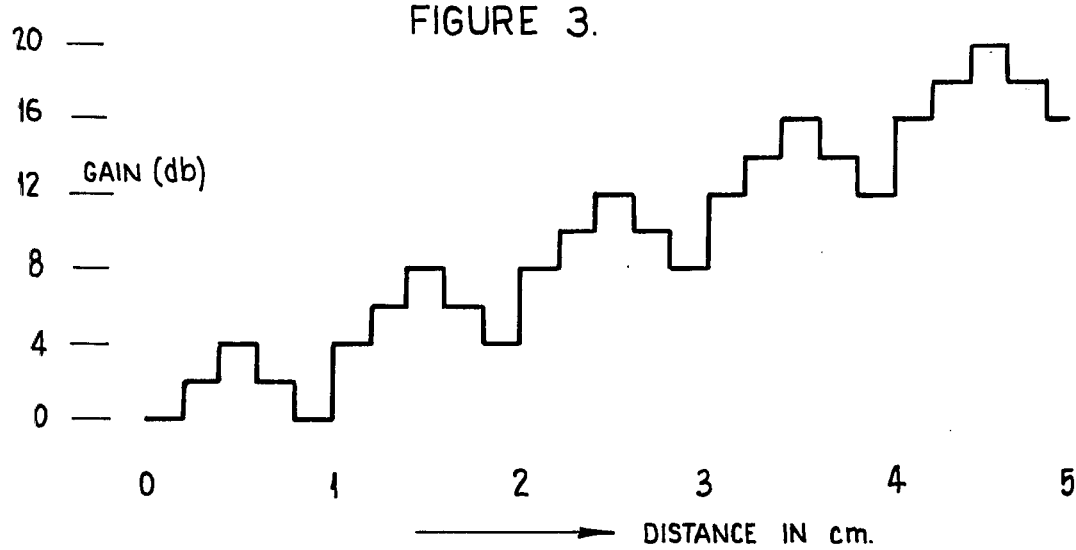
FIG. 3 shows the resultant characteristic when the gain variations of FIG. 1 and FIG. 2 are combined and it should be observed that the combined gain variation characteristic is no longer a monotonically rising characteristic but varies above and below the average value set by the characteristic of FIG. 1.
Figure 5:
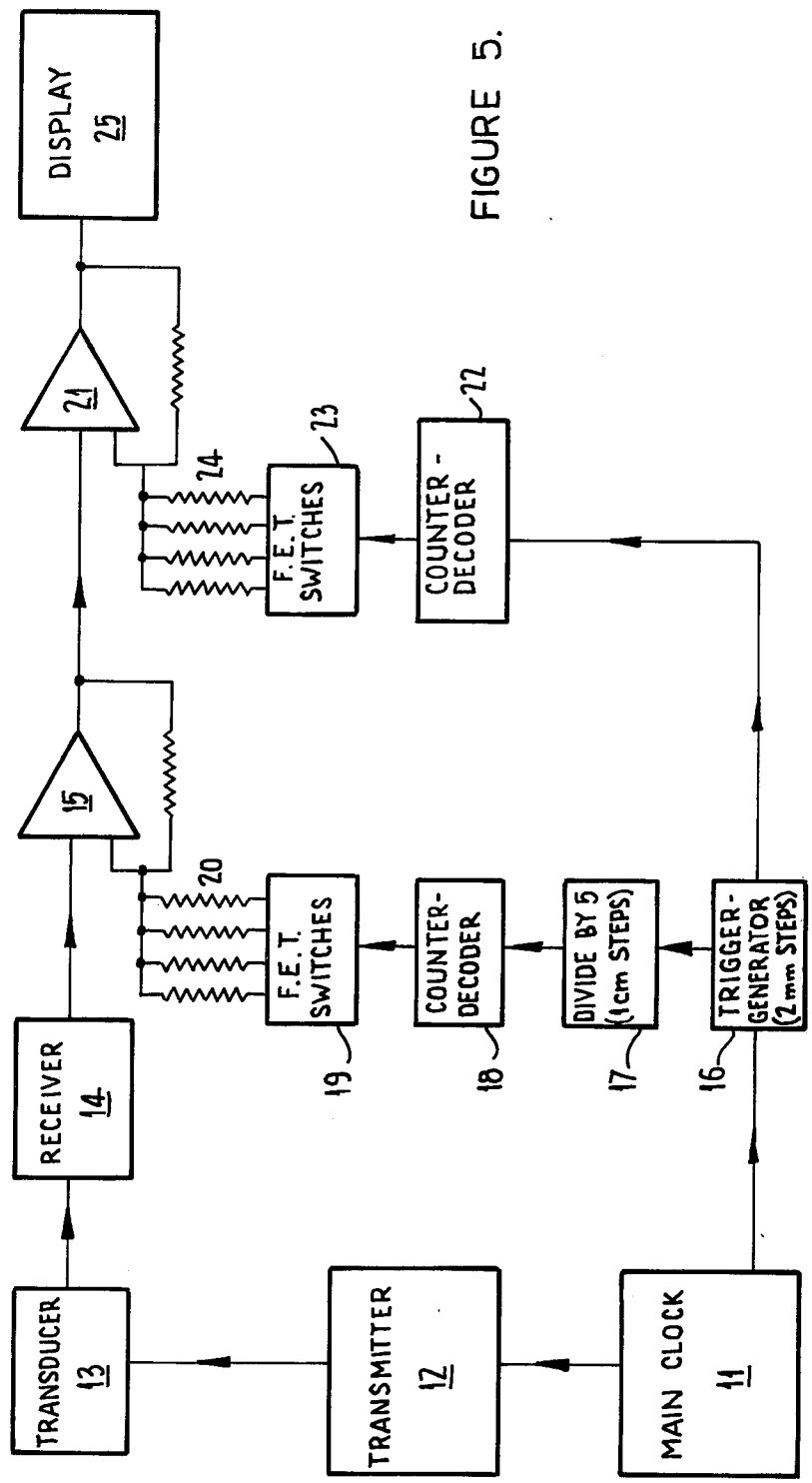

FIG. 5 is a block schematic diagram of one implementation of the invention. It is obvious to those skilled in the art that there are many ways of obtaining the gain characteristic shown by FIGS. 1 to 3. In the figure, one cycle of operation is initiated by a pulse from the main clock 11. This causes a pulse to be generated in the transmitter 12 which is fed to the transducer 13. A pulse of sound is propagated into the acoustic medium and echoes received from the same transducer 13. These echoes are pre-amplified in the reciever 14 then pass into the operational amplifier 15 which serves as time-again controlled amplifier. The same main clock pulse which generates a transmit pulse in the transducer 13 also starts the operation of trigger generator 16 which runs at an appropriate rate to generate pulses at intervals of 2mm in distance. These pulses are fed to the divide by 5 circuit 17 which then generates pulses corresponding to 1cm steps of distance. These are fed into the decoders 18 which control a band of field effect transducer switches 19 and feed back control resistors 20 which control the gain of the operational amplifier 15. The echo signals then pass to operational amplifier 21 which is similarly controlled in 2mm steps by counter decoder 22 and FET switches 23 and feed back resistors 24. The signal then passes to the display 25 in the usual manner. This technique may be used either with "A" or "B" mode. In the latter mode it is more readily applied with simple scanning since in that method of scanning each echo is scanned from one direction only. With compound scanning provision must be made for the number of times the echoes are scanned and suitable compensation made in the calculation of attenuation.

The claims defining the invention are as follows:

1. In a method of ultrasonic examination of an object comprising the steps of transmitting pulses of ultrasonic energy into the object, and receiving by receiver means echoes of said pulses of ultrasonic energy reflected by acoustic impedance discontinuites within the object, the improvement comprising:
    progressively increasing the gain of said receiver means in predetermined steps during the time between transmitter pulses to compensate for attenuation of said echoes within the object; and
    cyclically altering the gain of said receiver means during each of said predetermined steps by stepping the receiver gain through a cycle of discrete steps superimposed upon each of said predetermined steps.

2. A method as claimed in claim 1, further comprising adjusting said step-wise increase in gain of said receiver means by an adjustable stepped gain control.

3. A method as claimed in claim 1, wherein the gain of said receiver means is stepped in increments of predetermined and selectable gain and duration.

4. A method as claimed in claim 1, wherein said cyclic alteration of the gain of said receiver means comprises stepwise alteration of the gain around the value of the gain during each of the predetermined steps.

5. Apparatus for the ultrasonic examination of an object comprising:
    transmitter means for transmitting pulses of ultrasonic energy into the object; receiver means for receiving echoes of said pulses of ultrasonic energy reflected by acoustic impedance discontinuities within the object;
    means for increasing the gain of said receiver means in predetermined steps during the time between transmitter pulses to compensate for attenuation of said echoes within the object; and
    means for cyclically altering the gain of said receiver means during each of said predetermined steps by stepping the receiver gain through a cycle of discrete steps superimposed upon each of said predetermined steps.

6. Apparatus as claimed in claim 5, further comprising an adjustable stepped gain control for adjusting said step-wise increase in gain of said receiver means.

* * * * *